(12) United States Patent
Patangay et al.

(10) Patent No.: US 8,211,034 B2
(45) Date of Patent: Jul. 3, 2012

(54) MONITORING OF HEART SOUNDS

(75) Inventors: Abhilash Patangay, Inver Grove Heights, MN (US); Jeffrey E. Stahmann, Ramsey, MN (US); Robert J. Sweeney, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 731 days.

(21) Appl. No.: 11/777,739

(22) Filed: Jul. 13, 2007

(65) Prior Publication Data

US 2008/0119750 A1 May 22, 2008

Related U.S. Application Data

(63) Continuation-in-part of application No. 11/561,428, filed on Nov. 20, 2006, now abandoned.

(51) Int. Cl.
*A61B 5/02* (2006.01)

(52) U.S. Cl. ........................................... 600/528

(58) Field of Classification Search ........... 600/528–529
See application file for complete search history.

(56) References Cited

U.S. PATENT DOCUMENTS

| | | | |
|---|---|---|---|
| 4,094,308 A | 6/1978 | Cormier | |
| 4,289,141 A | 9/1981 | Cormier | |
| 4,773,401 A | 9/1988 | Citak et al. | |
| 5,190,035 A | 3/1993 | Salo et al. | |
| 5,685,317 A | 11/1997 | Sjostrom | |
| 5,687,738 A | 11/1997 | Shapiro et al. | |
| 5,697,375 A | 12/1997 | Hickey | |
| 5,792,195 A | 8/1998 | Carlson et al. | |
| 5,957,866 A | 9/1999 | Shapiro et al. | |
| 5,974,340 A | 10/1999 | Kadhiresan | |
| 6,064,910 A | 5/2000 | Andersson et al. | |
| 6,076,015 A | 6/2000 | Hartley et al. | |

(Continued)

FOREIGN PATENT DOCUMENTS

WO   WO-2008/063288 A2   5/2008

OTHER PUBLICATIONS

Carlson, Gerrard M., et al., "Managing Preload Reserve by Tracking the Ventricular Operating Point With Heart Sounds", U.S. Appl. No. 11/189,462, filed Jul. 26, 2005, 36 Pages.

(Continued)

*Primary Examiner* — Carl H Layno
*Assistant Examiner* — Paula J Stice
(74) *Attorney, Agent, or Firm* — Schwegman, Lundberg & Woessner, P.A.

(57) ABSTRACT

This document discusses, among other things, a system comprising an implantable medical device (IMD) including an implantable heart sound sensor circuit configured to produce an electrical heart sound signal representative of a heart sound of a subject and a processor circuit. The processor circuit is coupled to the heart sound sensor circuit and includes a detection circuit, a heart sound feature circuit and a trending circuit. The detection circuit configured to detect a physiologic perturbation and the heart sound feature circuit is configured to identify a heart sound feature in the electrical signal. The processor circuit is configured to trigger the heart sound feature circuit in relation to a detected physiologic perturbation. The trending circuit is configured to trend the heart sound feature in relation to a recurrence of the physiologic perturbation. The processor circuit is configured to declare a change in a physiologic condition of the patient according to the trending.

30 Claims, 8 Drawing Sheets

U.S. PATENT DOCUMENTS

| | | | |
|---|---|---|---|
| 6,161,042 A | 12/2000 | Hartley et al. | |
| 6,243,606 B1 * | 6/2001 | Mann et al. | 607/14 |
| 6,368,283 B1 | 4/2002 | Xu et al. | |
| 6,415,033 B1 | 7/2002 | Halleck et al. | |
| 6,463,326 B1 | 10/2002 | Hartley et al. | |
| 6,477,406 B1 | 11/2002 | Turcott | |
| 6,527,729 B1 * | 3/2003 | Turcott | 600/528 |
| 6,629,937 B2 | 10/2003 | Watrous | |
| 6,643,548 B1 * | 11/2003 | Mai et al. | 607/17 |
| 6,650,940 B1 * | 11/2003 | Zhu et al. | 607/28 |
| 6,741,886 B2 | 5/2004 | Yonce | |
| 6,868,346 B2 | 3/2005 | Larson et al. | |
| 6,949,075 B2 * | 9/2005 | Hatlesad et al. | 600/586 |
| 6,999,816 B2 * | 2/2006 | Van Bentem | 607/17 |
| 7,174,203 B2 * | 2/2007 | Arand et al. | 600/513 |
| 7,248,923 B2 | 7/2007 | Maile et al. | |
| 7,736,319 B2 | 6/2010 | Patangay et al. | |
| 7,853,327 B2 | 12/2010 | Patangay et al. | |
| 2002/0035337 A1 | 3/2002 | Oka | |
| 2003/0055461 A1 * | 3/2003 | Girouard et al. | 607/17 |
| 2003/0093003 A1 | 5/2003 | Watrous et al. | |
| 2004/0064056 A1 | 4/2004 | Ogura | |
| 2004/0127792 A1 * | 7/2004 | Siejko et al. | 600/439 |
| 2004/0138572 A1 | 7/2004 | Thiagarajan | |
| 2004/0167417 A1 | 8/2004 | Schulhauser et al. | |
| 2004/0215264 A1 | 10/2004 | Van Bentem | |
| 2004/0236239 A1 | 11/2004 | Murray et al. | |
| 2004/0254481 A1 * | 12/2004 | Brodnick | 600/484 |
| 2005/0102001 A1 | 5/2005 | Maile et al. | |
| 2005/0107838 A1 | 5/2005 | Lovett et al. | |
| 2005/0115561 A1 * | 6/2005 | Stahmann et al. | 128/200.24 |
| 2005/0137626 A1 | 6/2005 | Pastore et al. | |
| 2006/0020294 A1 | 1/2006 | Brockway et al. | |
| 2006/0047213 A1 | 3/2006 | Gavriely et al. | |
| 2007/0123943 A1 | 5/2007 | Patangay et al. | |
| 2008/0015651 A1 | 1/2008 | Ettori et al. | |
| 2008/0119749 A1 | 5/2008 | Haro et al. | |
| 2008/0125820 A1 | 5/2008 | Stahmann et al. | |
| 2008/0177191 A1 | 7/2008 | Patangay et al. | |
| 2008/0262368 A1 | 10/2008 | Patangay et al. | |
| 2011/0077543 A1 | 3/2011 | Patangay et al. | |

OTHER PUBLICATIONS

"U.S. Appl. No. 11/561,428, Non-Final Office Action mailed Apr. 20, 2010", 13 pgs.

"U.S. Appl. No. 11/736,055, Non-Final Office Action mailed Mar. 12, 2010", 8 pgs.

"U.S. Appl. No. 11/561,428, Response filed Oct. 20, 2010 to Non-Final Office Action mailed Apr. 20, 2010", 15 pgs.

"U.S. Appl. No. 11/736,055 Notice of Allowance mailed Aug. 13, 2010", 8 pgs.

"U.S. Appl. No. 11/736,055, Response filed Jul. 2, 2010 to Non-Final Office Action mailed Mar. 12, 2010", 17 pgs.

"U.S. Appl. No. 11/561,428, Final Office Action mailed Feb. 10, 2011", 19 pgs.

"U.S. Appl. No. 12/964,902, Non-Final Office Action Mailed Dec. 21, 2011", 8 pgs.

* cited by examiner

MONITORING OF HEART SOUNDS

RELATED APPLICATION

This document is a continuation-in-part of commonly assigned, Haro et al., U.S. patent application Ser. No. 11/561,428, entitled "Respiration-Synchronized Heart Sound Trending," which was filed Nov. 20, 2006, now abandoned, and which is incorporated by reference herein.

BACKGROUND

Implantable medical devices (IMDs) are devices designed to be implanted into a patient. Some examples of these devices include cardiac function management (CFM) devices such as implantable pacemakers, implantable cardioverter defibrillators (ICDs), cardiac resynchronization devices, and devices that include a combination of such capabilities. The devices are typically used to treat patients using electrical or other therapy and to aid a physician or caregiver in patient diagnosis through internal monitoring of a patient's condition. The devices may include one or more electrodes in communication with sense amplifiers to monitor electrical heart activity within a patient, and often include one or more sensors to monitor one or more other internal patient parameters. Other examples of implantable medical devices include implantable diagnostic devices, implantable insulin pumps, devices implanted to administer drugs to a patient, or implantable devices with neural stimulation capability.

Heart sounds are associated with mechanical vibrations from activity of a patient's heart and the flow of blood through the heart. Heart sounds recur with each cardiac cycle and are separated and classified according to the activity associated with the vibration. The first heart sound (S1) can be thought of as the vibrational sound made by the heart during tensing of the mitral valve. The second heart sound (S2) can be thought of as marking the beginning of diastole. The third heart sound (S3) and fourth heart sound (S4) can be conceptualized as related to filling pressures of the left ventricle during diastole. Heart sounds are useful indications of proper or improper functioning of a patient's heart.

Overview

This document relates generally to systems, devices, and methods for monitoring one or more heart sounds. In example 1, a system includes an implantable medical device (IMD). The IMD includes an implantable heart sound sensor circuit configured to produce an electrical heart sound signal representative of a heart sound of a subject and a processor circuit. The processor circuit is coupled to the heart sound sensor circuit and includes a detection circuit, a heart sound feature circuit and a trending circuit. The detection circuit configured to detect a physiologic perturbation and the heart sound feature circuit is configured to identify a heart sound feature in the electrical signal. The processor circuit is configured to trigger the heart sound feature circuit in relation to a detected physiologic perturbation. The trending circuit is configured to trend the heart sound feature in relation to a recurrence of the physiologic perturbation. The processor circuit is configured to declare a change in a physiologic condition of the patient according to the trending.

In example 2, the heart sound feature circuit of example 1 is optionally configured to identify a plurality of candidate heart sound features. The processor circuit optionally includes a ranking circuit configured to rank the candidate heart sound features, and select a heart sound feature for trending according to the ranking.

In example 3, the ranking circuit of example 2 is optionally configured to rank the candidate features according to a physiologic condition of the subject.

In example 4, the IMD of examples 1-4 optionally includes a second implantable sensor circuit in electrical communication with the processor circuit. The implantable sensor circuit is configured to produce a second electrical sensor signal related to one or more physiologic cardiovascular events in the subject. The detection circuit of examples 1-4 is optionally configured to detect the physiologic perturbation from the second electrical sensor signal.

In example 5, the second implantable sensor circuit of example 4 optionally includes a cardiac signal sensing circuit configured to provide an electrical representative of an intrinsic cardiac signal of the subject. The detection circuit is optionally configured to detect a premature ventricular contraction (PVC) to trigger the heart sound feature circuit.

In example 6, the second implantable sensor circuit of example 4 optionally includes an activity sensor to provide a signal representative of a physical activity level of the subject. The detection circuit is optionally configured to detect that a physical activity level of the subject exceeds a threshold activity level from the signal to trigger the heart sound feature circuit.

In example 7, the second implantable sensor circuit of example 4 optionally includes a posture sensor, and the detection circuit is optionally configured to detect a change in posture of the subject to trigger the heart sound feature circuit.

In example 8, the second implantable sensor circuit of example 4 optionally includes a cardiac signal sensing circuit configured to provide an electrical representative of an intrinsic cardiac signal of the subject. The detection circuit is optionally configured to detect that a heart rate of the subject exceeds a threshold heart rate to trigger the heart sound feature circuit.

In example 9, the second implantable sensor circuit of example 4 optionally includes a respiration sensor to provide a signal representative of respiration of the subject. The detection circuit is optionally configured to detect a phase of a respiration cycle of the subject from the signal to trigger the heart sound feature circuit.

In example 10, the processor circuit of examples 1-9 optionally includes a timer circuit, and the processor circuit is optionally configured to trigger the heart sound feature circuit in relation to a time the subject receives a drug therapy.

In example 11, the processor circuit of examples 1-10 optionally includes a timer circuit, and the processor circuit is optionally configured to trigger the heart sound feature circuit in relation to a phase of a circadian cycle of the subject.

In example 12, the IMD of examples 1-11 optionally includes a therapy circuit in electrical communication with the processor circuit. The therapy circuit is configured to provide a therapy to the subject, and the processor circuit is optionally configured to initiate a therapy to cause the physiologic perturbation and to trigger the heart sound feature circuit in a time relation to the therapy.

In example 13, the processor circuit of example 12 is optionally configured to initiate a paced cardiac contraction as the physiologic perturbation and to trigger the heart sound feature circuit in a time relation to the paced cardiac contraction.

In example 14, the processor circuit of examples 12 and 13 is optionally configured to initiate a premature ventricular contraction (PVC) as the physiologic perturbation and to trigger the heart sound feature circuit in a time relation to the PVC.

In example 15, a method includes sensing an electrical heart sound signal representative of a heart sound of a subject in relation to a physiologic perturbation using an IMD, identifying a feature of the heart sound signal, trending the feature of the heart sound signal in relation to a recurrence of the physiologic perturbation, and identifying a change in a physiologic condition of the subject from the trending.

In example 16, identifying the feature of example 15 optionally includes identifying a plurality of candidate features of the heart sound signal, ranking the candidate features, and selecting a feature for trending according to the ranking.

In example 17, ranking the candidate features of example 16 optionally includes ranking the candidate features according to a physiologic condition of the subject.

In example 18, identifying the feature of the heart sound signal of examples 15-17 optionally includes triggering identification of the feature of the heart sound in relation to a detected physiologic perturbation.

In example 19, identifying the feature of the heart sound signal of examples 15-18 optionally includes triggering identification of the feature of the heart sound in relation to an induced physiologic perturbation.

In example 20, the physiologic perturbation of examples 15-19 optionally includes a premature ventricular contraction (PVC), and identifying the feature of the heart sound signal optionally includes sensing a heart sound signal includes sensing a heart sound signal in relation to the PVC.

In example 21, the physiologic perturbation of examples 15-20 optionally includes a change in posture of the subject, and sensing the heart sound signal optionally includes sensing a heart sound signal in relation to the change in posture.

In example 22, the physiologic perturbation of examples 15-21 optionally includes a heart rate of the subject exceeding a threshold heart rate, and sensing the heart sound signal optionally includes sensing a heart sound signal in relation to the heart rate of the subject exceeding the threshold heart rate.

In example 23, the physiologic perturbation of examples 15-22 optionally includes the subject receiving drug therapy, and sensing the heart sound signal optionally includes sensing a heart sound signal in relation to a time the subject receives the drug therapy.

In example 24, the physiologic perturbation of examples 15-23 optionally includes a paced cardiac contraction, and sensing the heart sound signal optionally includes sensing the heart sound signal in relation to the paced cardiac contraction.

In example 25, the physiologic perturbation of examples 15-24 optionally includes a phase of a respiration cycle, and sensing the heart sound signal optionally includes sensing the heart sound signal in relation to the phase of a respiration cycle.

In example 26, the physiologic perturbation of examples 15-25 optionally corresponds to a circadian pattern, and the sensing the heart sound signal optionally includes sensing the heart sound signal in relation to the circadian pattern.

In example 27, the physiologic perturbation of examples 15-26 optionally includes activity of the subject exceeding a threshold activity level, and sensing the heart sound signal optionally includes sensing the heart sound signal in relation to the activity level of the subject exceeding the threshold activity level.

In example 28, a system includes means for implantably sensing an electrical heart sound signal representative of a heart sound of a subject, means for identifying a feature of the heart sound signal in relation to a detected physiologic perturbation, means for trending the feature of the heart sound signal in relation to a recurrence of the physiologic perturbation, and means for identifying a change in a physiologic condition of the subject from the trending.

In example 29, a system example includes an IMD and an external device. The IMD includes an implantable heart sound sensor circuit configured to produce an electrical heart sound signal representative of a heart sound of a subject and a first processor circuit coupled to the heart sound sensor circuit. The processor circuit includes a detection circuit configured to detect a physiologic perturbation; and a heart sound feature circuit configured to identify a heart sound feature in the electrical signal. The processor circuit is configured to trigger the heart sound feature circuit in relation to a detected physiologic perturbation. The external device includes a second processor circuit which includes a trending circuit configured to trend the heart sound feature in relation to a recurrence of the physiologic perturbation. The second processor circuit is configured to declare a change in a physiologic condition of the patient according to the trending.

In example 30, the heart sound feature circuit of example 29 is optionally configured to identify a plurality of candidate heart sound features. The first processor circuit is optionally configured to communicate information about the heart sound signal features to the external device. The second processor circuit optionally includes a ranking circuit configured to rank the candidate heart sound features, and select a heart sound feature for trending according to the ranking.

In example 31, the ranking circuit of example 30 is optionally configured to rank the candidate features according to a physiologic condition of the subject.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Because heart sounds are a mechanical measure of a patient's hemodynamic system, monitoring of one or more heart sounds can aid a caregiver in detecting overall progression of heart disease.

Figure 1:
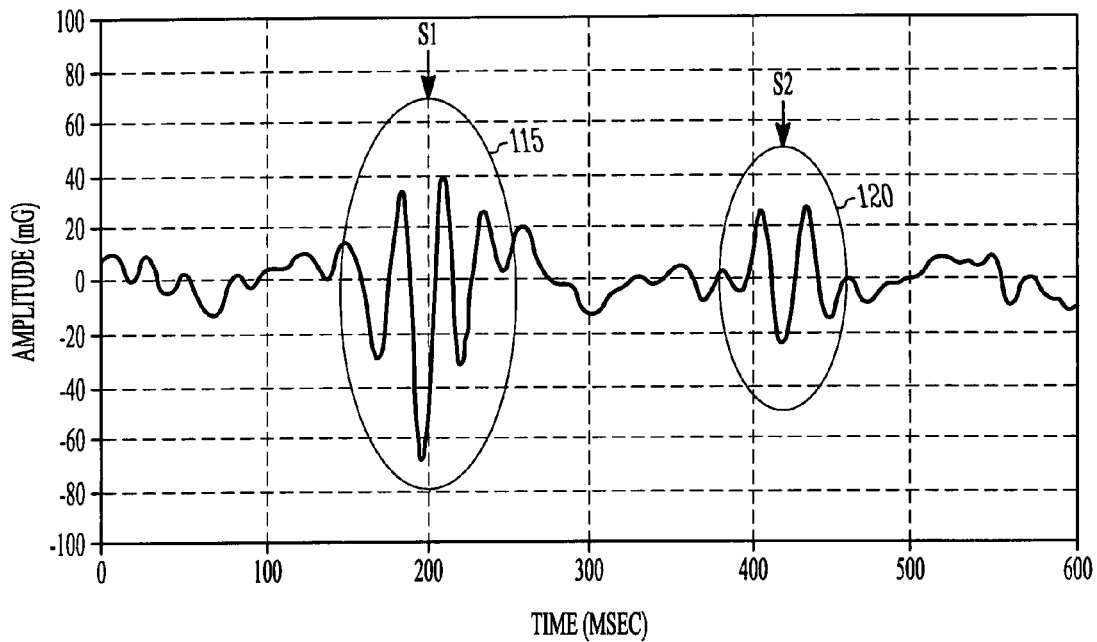
FIG. 1 is an illustration of a graph of S1 and S2 heart sounds.

FIG. 1 is an illustration of a graph of the S1 115 and S2 120 heart sounds. The mechanical events indicated by heart sounds change when there is a physiologic or patho-physiologic change in the cardiovascular system. These changes can be viewed as physiologic perturbations. For example, when a patient exercises, their heart rate and cardiac stroke volume increases. The increase in heart rate decreases the cardiac cycle length and shifts the S1 and S2 heart sounds in time. The increase in stroke volume changes the amplitudes of the S1 and S2 heart sounds. Other examples of such physiologic perturbations include, without limitation, a change in patient posture, one or more premature ventricular contractions (PVCs), drug therapy received by the patient, a paced cardiac contraction, and the inhaling or exhaling of the patient. A specific perturbation causes an expected change in the heart sounds. Monitoring heart sounds when the specific perturbation occurs may provide additional information about the physiologic condition of the patient or subject.

Figure 2:
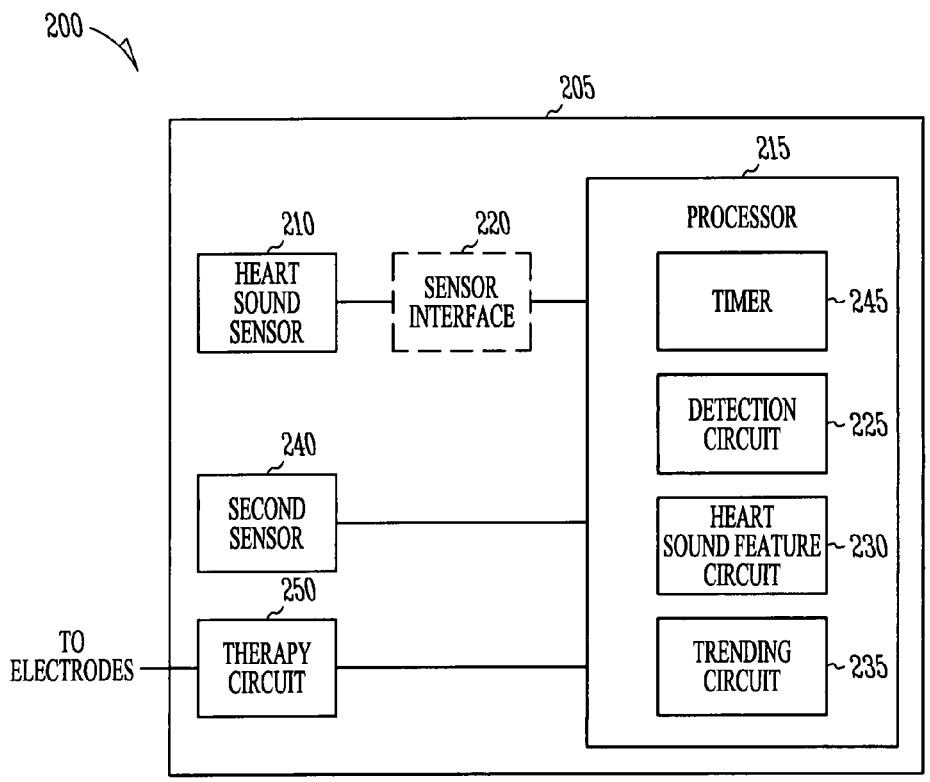
FIG. 2 shows a block diagram of portions of an example of a system for monitoring one or more heart sounds.

FIG. 2 shows a block diagram of portions of an example of a system 200 for monitoring one or more heart sounds. The system 200 includes an implantable medical device (IMD) 205 that in turn includes a heart sound sensor circuit 210. Heart sound sensors generally include implantable acoustic sensors that convert the detected sounds of the heart into an electrical signal representative of the heart sounds. In some examples, the heart sound sensor circuit 210 includes an accelerometer located within a hermetically sealed canister or "can" of the IMD 205. In another sensor example, a microphone is located within the IMD can. In another example, the heart sound sensor circuit 210 includes a strain gauge.

The system 200 also includes a processor circuit 215 coupled to the heart sound sensor circuit 210. In some examples, the processor circuit 215 is coupled to the heart sound sensor circuit 210 through a heart sound sensor interface circuit 220. The heart sound sensor interface circuit 220 provides signal conditioning such as signal filtering and/or amplification for example.

The processor circuit 215 includes a detection circuit 225, a heart sound feature circuit 230, and a trending circuit 235. The processor circuit 215 can be implemented using hardware circuits, firmware, software or any combination of hardware, firmware and software. Examples, include a microprocessor, a logical state machine, and a processor such as a microprocessor, application specific integrated circuit (ASIC), or other type of processor. The processor circuit 215 is configured to perform or execute a function or functions. Such functions correspond to circuits or other type of modules, which are software, hardware, firmware or any combination thereof. Multiple functions may be performed in one or more of the circuits.

The detection circuit 225 detects a physiologic perturbation. When a perturbation is detected, the processor circuit 215 triggers the heart sound feature circuit 230 in relation to the perturbation to identify a heart sound feature in the electrical signal representative of the heart sound.

In some examples, the detection circuit 225 detects the physiologic perturbation using the electrical signal from the heart sound sensor circuit 210. For example, if the physiologic perturbation is patient exercise, the detection circuit 225 may detect exercise from a shift in S1 and S2 heart sounds. If the heart sound sensor circuit 210 includes an accelerometer, the accelerometer may double as an activity sensor and the detection circuit 225 may detect patient activity such as exercise using the accelerometer. Descriptions of systems to monitor heart and detect patient activity may be found in Maile et al., U.S. Patent Application Publication No. 20050102001, entitled "Dual-Use Sensor for Rate Responsive Pacing and Heart Sound Monitoring, filed Nov. 6, 2003, now issued as U.S. Pat. No. 7,248,923, which is incorporated herein by reference.

According to some examples, the detection circuit 225 may detect the physiologic perturbation using a second implantable sensor circuit 240. The second implantable sensor circuit 240 produces a second electrical sensor signal related to one or more physiologic cardiovascular events in the subject. For example, if the physiologic perturbation is patient exercise, the second implantable sensor circuit 240 includes an activity sensor to provide a signal representative of an activity level of the subject, such as an accelerometer for example. The detection circuit 225 is configured to detect that a physical activity level of the subject exceeds a threshold activity level from the signal.

As described above, when a patient exercises, their heart rate and cardiac stroke volume increases. The increase in heart rate decreases the cardiac cycle length and shifts the S1 and S2 heart sounds in time. The increase in stroke volume due to the exercise changes the amplitudes of the S1 and S2 heart sounds. Therefore, a shift in the S1 and S2 heart sounds and an increase in amplitudes of one or both heart sound are features that correlate to stroke volume and can be used to monitor a physiologic change in stroke volume.

In some examples, the physiologic perturbation is a change in posture of the patient. The second implantable sensor circuit 240 includes a posture sensor and the detection circuit 225 is configured to detect a change in posture of the subject. Changes in contractility of the subject's heart are reflected in heart sounds. A change in posture changes the preload of the heart. A change in contractility may be reflected in a change in timing intervals of the heart sounds and/or in the amplitude of the S1 heart sound. For example, in a weak left ventricle the isovolumic contraction time is prolonged; resulting in a wide S1 complex or long S1 duration. Also, the occurrence of the S1 complex may be delayed. Therefore, S1 width, S1 amplitude, and a time shift in S1 are features that correlate to contractility and can be used to monitor a physiologic change in contractility.

In some examples, the physiologic perturbation is a change in phase of a circadian cycle or pattern of the subject, (e.g., waking or sleeping). The processor circuit 215 may include a timer circuit 245. The processor circuit 215 triggers the heart sound feature circuit to identify a heart sound feature in relation to a phase of a circadian pattern of the subject.

In some examples, the physiologic perturbation is a drug therapy received by the subject. If the heart sounds change (e.g., amplitude) in response to a drug therapy (e.g., a diuretic intake), this may indicate that the renal function is not resistant to the drug therapy. Therefore, a change in amplitude of heart sounds may be a feature that correlates to a drug therapy's impact on renal function. In certain examples, the processor circuit uses the timer circuit 245 to trigger the heart sound feature circuit in relation to a time the subject receives the drug therapy. In some examples, the IMD 205 includes a drug reservoir and administers a drug therapy to the subject such as by a positive displacement pump mechanism for example. The processor circuit 215 triggers the heart sound feature circuit in a time relation to a delivery of drug therapy to the subject.

Figure 3:
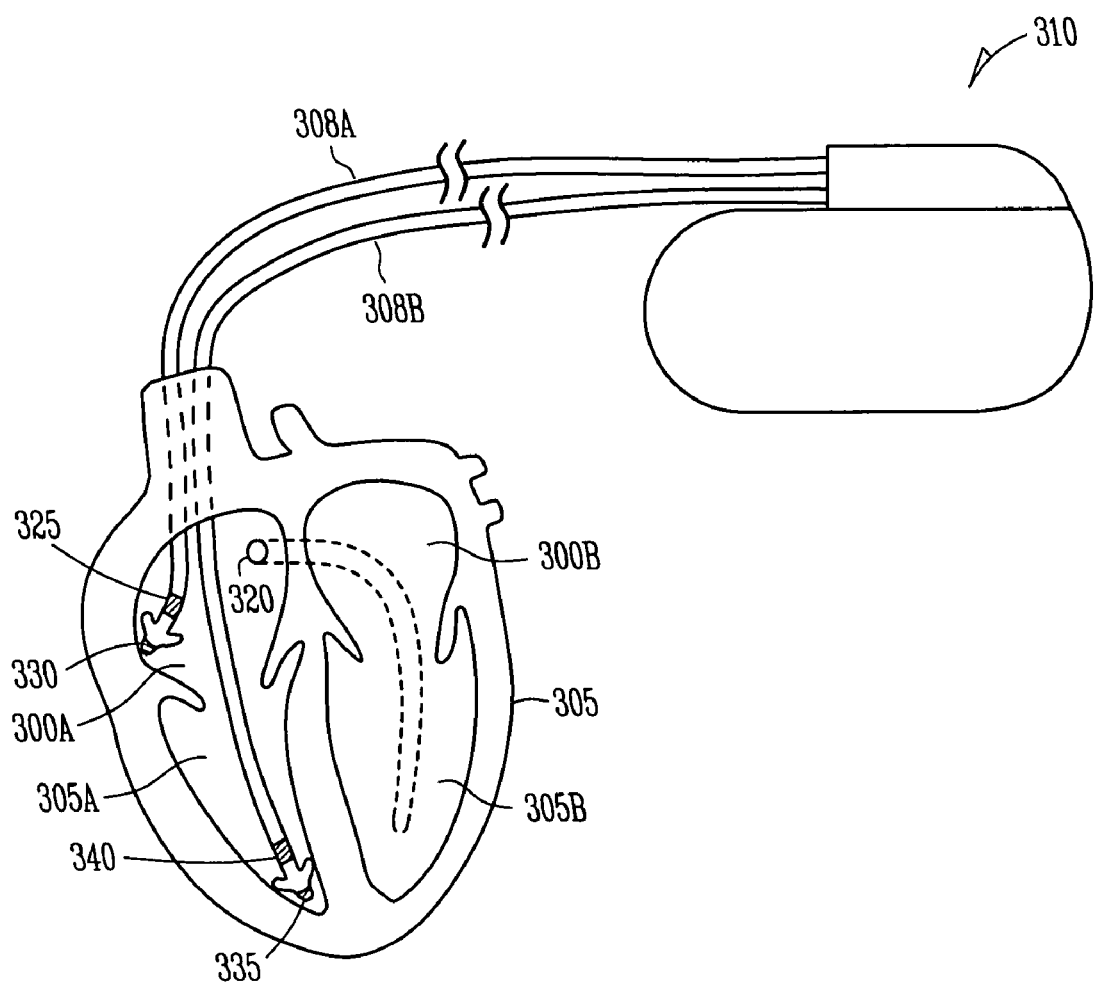
FIG. 3 illustrates an example of an IMD coupled to a heart by one or more leads.

FIG. 3 illustrates an example of an IMD 310 coupled to heart 305, such as by one or more leads 308A-B. Heart 305 includes a right atrium 300A, a left atrium 300B, a right ventricle 305A, a left ventricle 305B, and a coronary vein 320 extending from right atrium 300A. In this embodiment, atrial lead 308A includes electrodes (electrical contacts, such as ring electrode 325 and tip electrode 330) disposed in, around, or near a right atrium 300A of heart 305 for sensing signals, or delivering pacing therapy, or both, to the right atrium 300A. Lead 308A optionally also includes additional electrodes, such as for delivering atrial cardioversion, atrial defibrillation, ventricular cardioversion, ventricular defibrillation, or combinations thereof to heart 305. Lead 308A optionally further includes additional electrodes for delivering pacing or resynchronization therapy to the heart 305.

Ventricular lead 308B includes one or more electrodes, such as tip electrode 335 and ring electrode 340, for sensing signals, for delivering pacing therapy, or for both sensing signals and delivering pacing therapy. Lead 308B optionally also includes additional electrodes, such as for delivering atrial cardioversion, atrial defibrillation, ventricular cardioversion, ventricular defibrillation, or combinations thereof to heart 305. Such electrodes typically have larger surface areas than pacing electrodes in order to handle the larger energies involved in defibrillation. Lead 308B optionally further includes additional electrodes for delivering pacing or resynchronization therapy to the heart 305.

Other forms of electrodes include meshes and patches which may be applied to portions of heart 305 or which may be implanted in other areas of the body to help "steer" electrical currents produced by IMD 310. In one embodiment, one of atrial lead 308A or ventricular lead 308B is omitted, i.e., a "single chamber" device is provided, rather than the dual chamber device illustrated in FIG. 3. In another embodiment, additional leads are provided for coupling the IMD 310 to other heart chambers and/or other locations in the same heart chamber as one or more of leads 308A-B. The present methods and systems will work in a variety of configurations and with a variety of electrical contacts or "electrodes," including a leadless system that uses electrodes remote from, rather than touching, the heart 305.

Returning to FIG. 2, in some examples, the second implantable sensor circuit 240 includes a cardiac signal sensing circuit. The cardiac signal sensing circuit includes one or more sense amplifiers in electrical communication with electrodes to provide an electrical representative of an intrinsic cardiac signal of the subject.

Baroreflex sensitivity (BRS) is a measure of the gain in the resulting recovery in blood pressure and is typically measured using units of milliseconds per millimeters of mercury (ms/mmHg). BRS has been shown to be a good prognostic indicator. For example, Mean arterial pressure (MAP) recovery is used to assess a patient's hemodynamic tolerance to a tachyarrhythmia. BRS correlates well to MAP recovery during ventricular tachyarrhythmia and for this reason BRS is a good measure of hemodynamic stability during tachyarrhythmia. An indication of a subject's BRS can be established by measuring blood pressure and monitoring heart rate.

In certain examples, the physiologic perturbation includes a sensed premature ventricular contraction (PVC) and the detection circuit 225 is configured to detect a PVC. A PVC refers to two ventricular contractions occur (V-V interval), without an intervening a trial contraction. An indication of BRS indicator is a measure of the gain in the resulting recovery in blood pressure after the PVC. The gain can be viewed as the slope of a graph of V-V intervals versus change in blood pressure. A higher slope reflects higher BRS and a lower slope reflects lower BRS. Descriptions of systems and methods that monitor the baroreflex sensitivity of a subject are found in Ettori et al., U.S. patent application Ser. No. 11/457,644, "Baroreflex Sensitivity Monitoring and Trending for Tachyarrhythmia Detection," filed Jul. 14, 2006, published as U.S. Patent Application Publication No. 20080015651, which is incorporated herein by reference.

A change in blood pressure may be reflected in a change in heart sounds such as the amplitude of the heart sounds and/or the power spectrum of the heart sounds for example. Therefore, heart sound amplitude and heart sound power spectrum are features that correlate to blood pressure and can be used as a surrogate to monitor a physiologic change in BRS.

In certain examples, the physiologic perturbation includes a heart rate that exceeds a threshold heart rate, and the detection circuit 225 is configured to detect when a heart rate of the subject exceeds a threshold heart rate value. A change in one or more heart sound intervals are features that are useful to monitor heart rate variability.

According to some examples, the physiologic perturbation includes modulation of the subject's hemodynamics due to respiration. In certain examples, the second implantable sensor circuit 240 includes a respiration sensor to provide a signal representative of respiration of the subject, and the detection circuit 225 is configured to detect a phase of a respiration cycle of the subject from the signal. An example of an implantable respiration sensor is a transthoracic impedance sensor to measure minute respiration volume. An approach to measuring transthoracic impedance is described in Hartley et al., U.S. Pat. No. 6,076,015, "Rate Adaptive Cardiac Rhythm Management Device Using Transthoracic Impedance," filed Feb. 27, 1998, which is incorporated herein by reference.

Modulation of hemodynamics due to respiration is another example of a physiologic perturbation that changes heart sounds. During end-inspiration, the cardiac stroke volume may increase which in turn increases heart sound amplitude. Also, an increase in cardiac stroke volume shifts the timing of the opening and closing of the cardiac valves and hence shifts the timing of the heart sounds.

Figure 4:
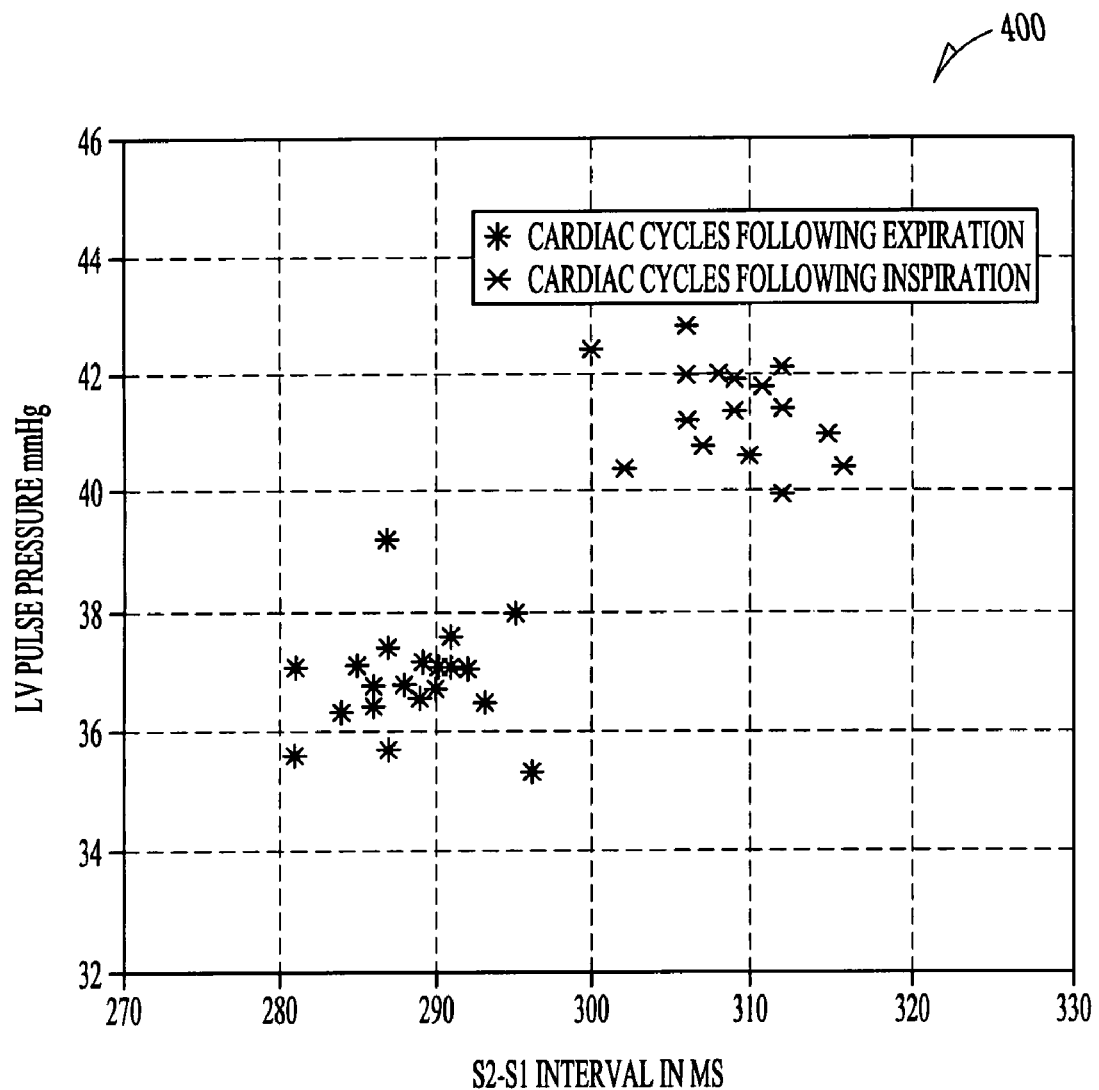
FIG. 4 shows a graph illustrating S2-S1 time intervals for inspiration and expiration.

FIG. 4 shows a graph 400 illustrating S2-S1 time intervals for inspiration and expiration. The graph 400 shows that the S2-S1 time interval is longer after inspiration than expiration. This difference is time intervals is due to a change in stroke volume and is also reflected in a difference in left ventricle (LV) pressure. The graph shows that LV pressure is higher for inspiration, and thus the amplitude of the S2 and S1 heart sounds will be greater for inspiration. Therefore, the S2-S1 interval and the heart sound amplitude are features that correlate to stroke volume and can be used to monitor a physiologic change in stroke volume. Descriptions of systems and methods for monitoring heart sounds in relation to respiration are found in the above mentioned Haro et al., "Respiration-Synchronized Heart Sound Trending," which is incorporated herein by reference.

As described above, heart sound features may correlate to a drug therapy's impact on renal function. A drug therapy's impact on renal function may also be reflected in a change in thoracic impedance. Thus, measuring transthoracic impedance in conjunction with monitoring heart sounds is useful to monitor a drug therapy's impact on renal function.

When a perturbation is detected using the detection circuit 225 of FIG. 2, the processor circuit 215 triggers the heart sound feature circuit 230 in relation to the perturbation to identify a heart sound feature in the electrical signal representative of the heart sound. Examples of heart sound features include, without limitation, an interval between heart sounds (e.g., an interval between the S1 and the S2 heart sounds in FIG. 1), a duration of a heart sound (e.g., the duration or width of the S1 heart sound), an amplitude of a peak of a heart sound (e.g., a zero-to-peak amplitude or a peak-to-peak amplitude of a heart sound) or a power spectrum of a heart sound. Descriptions of systems and methods for additional heart sound measurements are found in Patangay et al., U.S. patent application Ser. No. 11/625,003, "Ischemia Detection Using Heart Sound Timing," filed Jan. 19, 2007, published as U.S. Patent Application Publication No. 20080177191, now issued as U.S. Pat. No. 7,736,319, which is incorporated by reference.

The trending circuit 235 trends the identified heart sound features in relation to a recurrence of the physiologic perturbation. The goal is to choose a heart sound feature providing the desired information about the patient, identify the feature in relation to the physiologic perturbation using the heart sound feature circuit 230, and trend the feature over time to determine whether there is a change in a physiologic condition of the patient according to the trending. The trending determines a measurable margin of change in an aspect of the pathological condition to uncover a subclinical pathologic change. Examples of the trending include, without limitation, trending to determine a change in decompensation (heart failure), a change in sympathetic activity, a change in patient response to a drug therapy, and a change in cardiac contractility.

In some examples, the IMD 205 includes a communication circuit to communicate information wirelessly to an external device, such as by mutual induction, radio frequency (RF), or another telemetry method. The IMD 205 communicates an indication of the change in the physiologic condition to an external device. The indication is then available to a user, such as a clinician or caregiver, or is available to a third device in communication with the external device.

In some examples, the IMD does not necessarily include the trending circuit 235, and the trending is done by the external device, such as an IMD programmer or a server that is part of a patient management system. The IMD 205 includes a communication circuit to communicate information about one or more heart sound features to the external device. The external device trends a feature over time to determine whether there is a change in a physiologic condition of the patient according to the trending.

The physiologic perturbation used to trigger the feature identification of the heart sound signal may be sensed and occur naturally, or the perturbation may be induced. The perturbation may be induced by causing some action by the subject (e.g., forced breathing by the patient to cause a PVC) or the perturbation may be induced by the IMD 205. In some examples, the IMD 205 includes a therapy circuit 250. The therapy circuit 250 provides a therapy (e.g., pacing therapy) to the subject. The processor circuit 215 initiates a therapy to induce the physiologic perturbation and to trigger the heart sound feature circuit 230 in a time relation to the therapy.

A pacing pulse provided by the therapy circuit 250 can be viewed as an induced PVC. For example, the processor circuit 215 may initiate two ventricular contractions or a ventricular contraction after an intrinsic ventricular contraction before an intervening atrial contraction occurs. The processor circuit 215 initiates the PVC and triggers the heart sound feature circuit 230 in a time relation to the PVC. Thus, heart sound features can be monitored in relation to a PVC without having to wait for a sensed occurrence of a PVC.

Because pacing therapy may cause a change in synchrony of a cardiac contraction, pacing therapy is also a physiologic perturbation. If the chambers (e.g., the ventricles) of the heart are dyssynchronous, pacing synchronizes the contraction by activating delayed myocardial regions with those regions that activate earlier. Subjects with heart failure (HF) may have a dyssynchrony of heart chambers. Pacing the chambers to restore coordination of the contractions increases the stroke volume of the heart and therefore changes the heart sounds.

Figure 5:
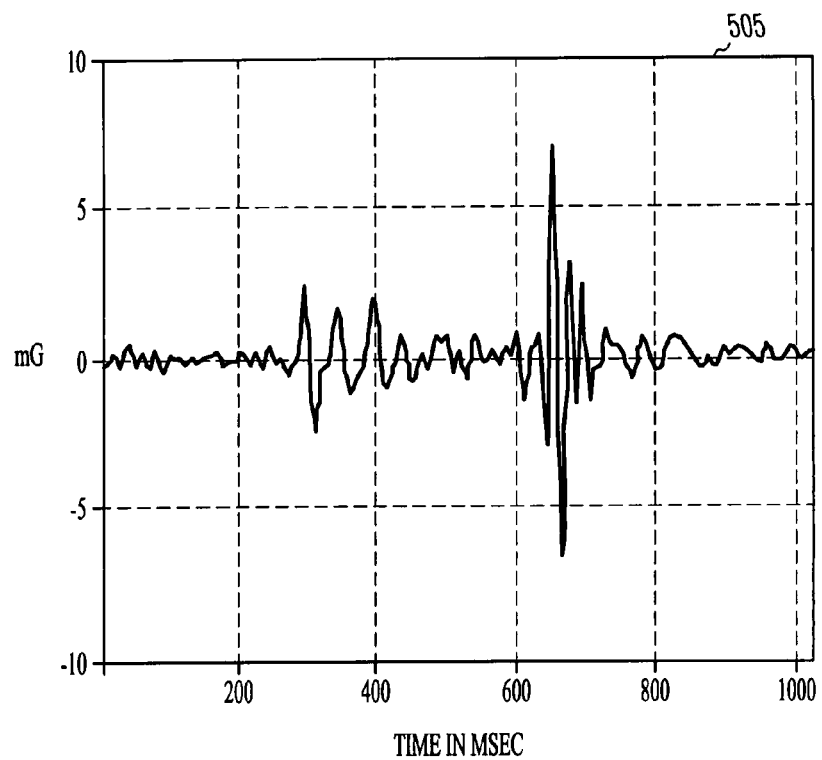
FIG. 5 shows a graph illustrating S1 and S2 heart sounds without pacing the left ventricle (LV), and a graph illustrating heart sounds with pacing the LV.
Figure 5:
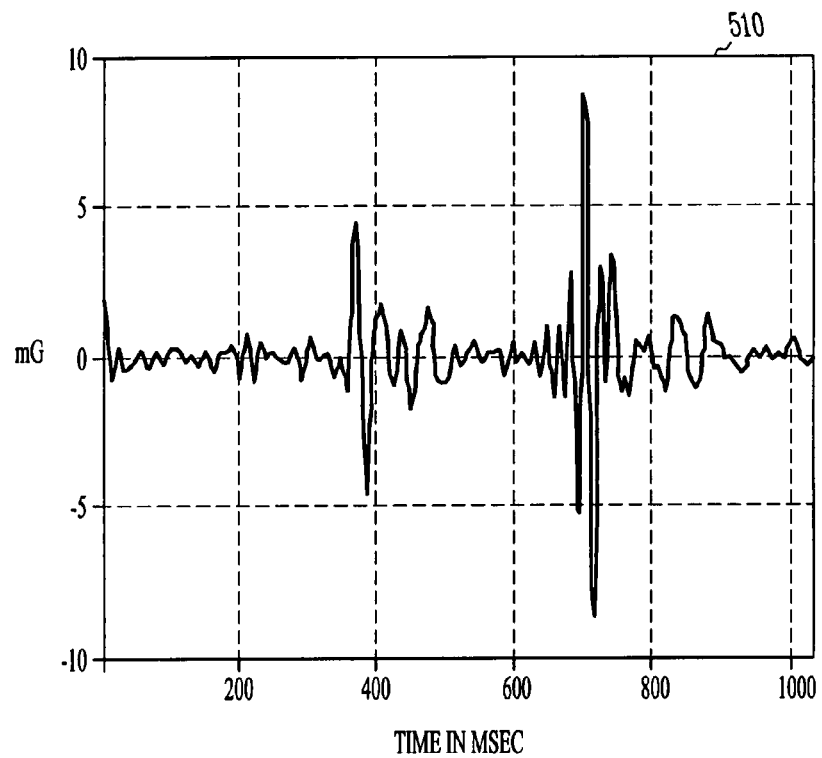

FIG. 5 shows a graph 505 illustrating S1 and S2 heart sounds without pacing the left ventricle (LV) to synchronize contractions with the right ventricle (RV), and a graph 510 illustrating heart sounds with pacing to synchronize the LV with the RV. It can be seen in the graphs that pacing the left ventricle synchronous with the right ventricle increases the amplitude of the S1 and S2 heart sound. In the IMD of FIG. 2, the processor circuit 215 initiates a paced cardiac contraction as the physical perturbation and triggers the heart sound feature circuit 230 in a time relation to the paced cardiac contraction.

Figure 6:
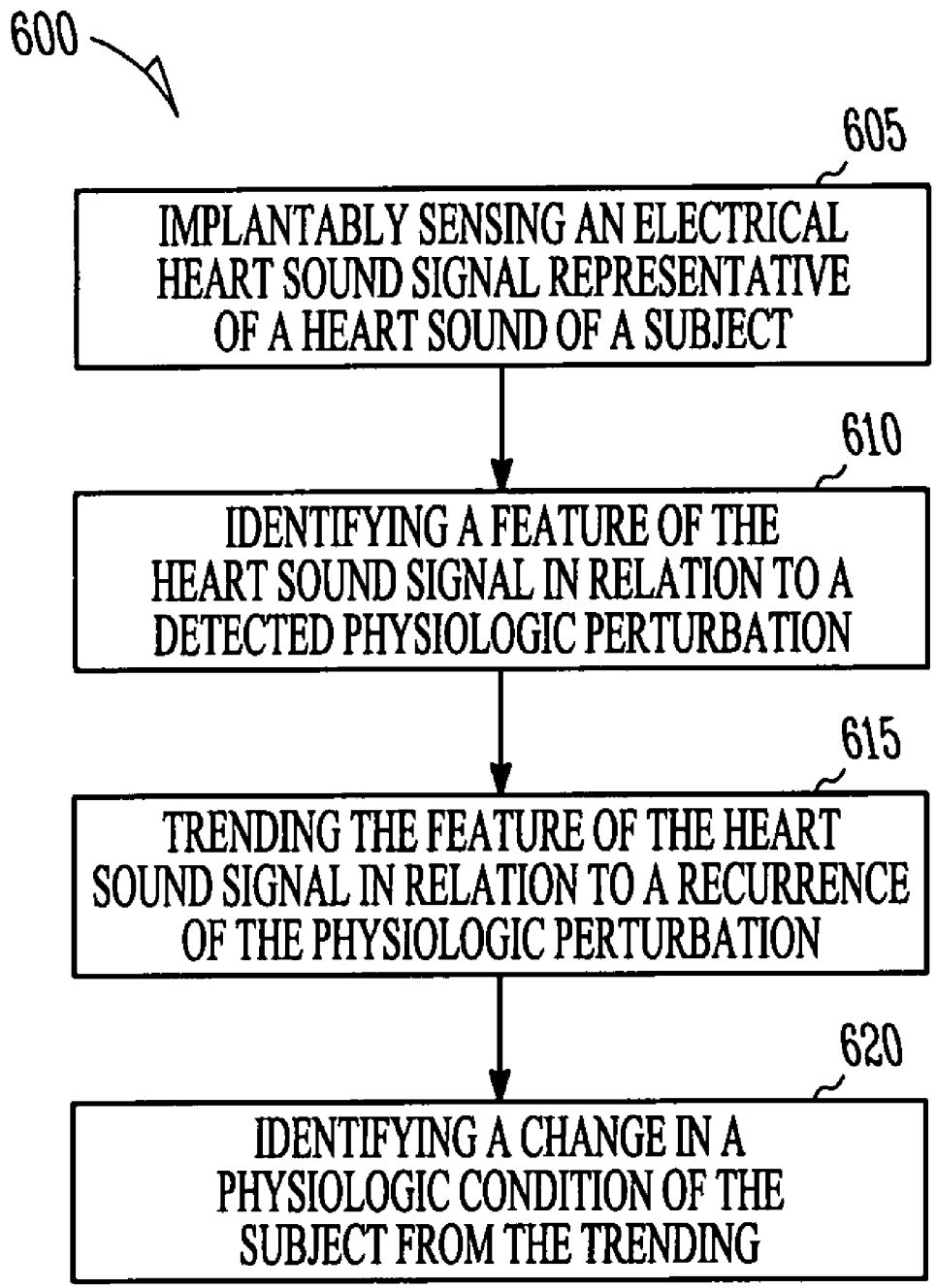
FIG. 6 shows a flow diagram of an example of a method for monitoring heart sounds.

FIG. 6 shows a flow diagram of an example of a method 600 for monitoring heart sounds. At 605, an electrical heart sound signal representative of a heart sound of a subject is implantably sensed. At 610, a feature of the heart sound signal is identified in relation to a detected physiologic perturbation. At 615, the feature is trended in relation to a recurrence of the physiologic perturbation. At 620, a change in a physiologic condition of the subject is identified from the trending.

Many heart sound features have been described as being of interest to different physiologic pathologies. A non-exhaustive list of these features have included durations of heart sounds, intervals between heart sounds, amplitudes of heart sounds and power spectrums of heart sounds. Thus, heart sounds have multiple components or features and the features may be represented in the time domain or the frequency domain.

Figure 7:
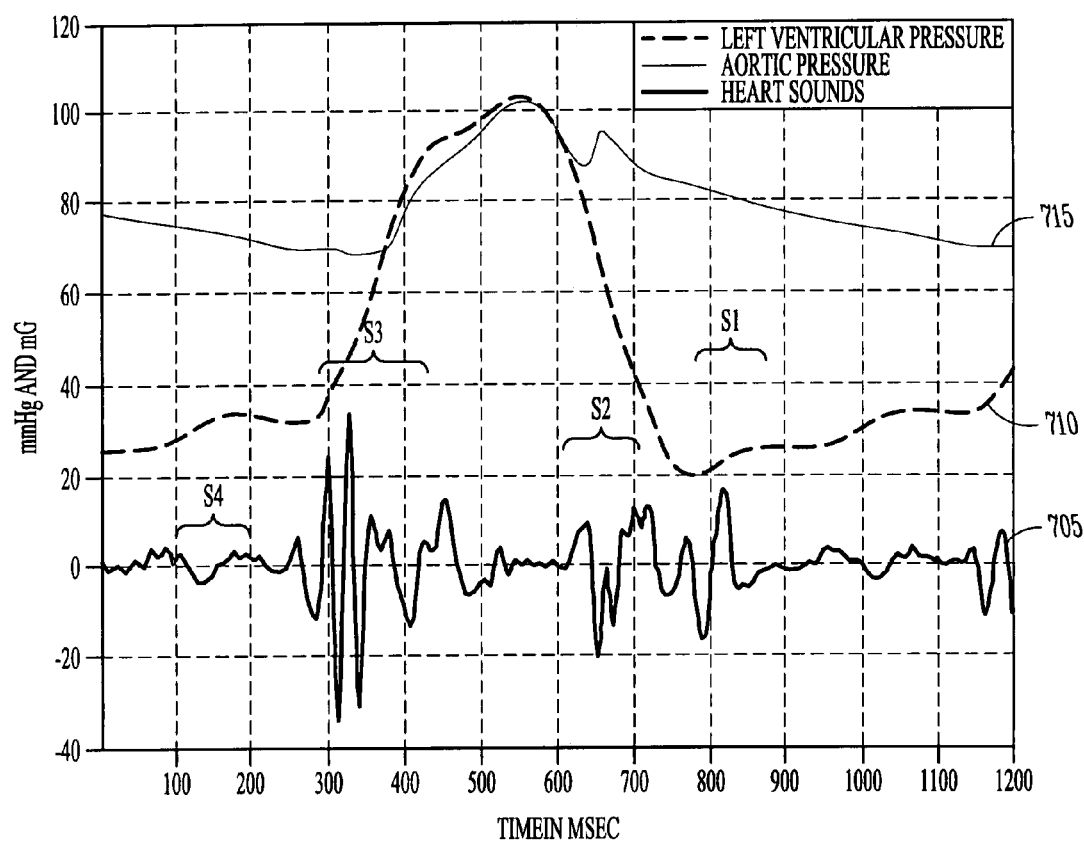
FIG. 7 shows a heart sound graph of S1-S4 heart sounds recorded synchronously with a LV pressure graph and an aortic pressure graph.

FIG. 7 shows a heart sound graph 705 of the S1-S4 heart sounds recorded synchronously with a LV pressure graph 710 and an aortic pressure graph 715. It can be seen in the graphs that the different components of the S1 waveform have different frequency localization properties. For example, the early portion of S1, associated with the mitral valve has a higher frequency than the later portion of the S1 heart sound associated with blood ejecting after opening of the aortic valve. The mitral component is typically localized around 30-60 hertz (Hz) whereas the aortic component is typically localized around 15-25 Hz.

While there is much information regarding the localization and amplitudes of various heart sounds components contained in the time-frequency domain of heart sounds, this information is not consistent across different patho-physiologic states. For example, in patients with reduced contractility with mitral regurgitation, the mitral component of the S1 heart sound is diminished due to leaky valves. Each patient or subject may have a unique pathology that giving the heart sounds of the patient a unique time-frequency footprint with patho-physiologic information related to the patient's disease state. This time-frequency footprint contains information that, when extracted, can be used for clinical applications.

Wavelet filtering can be used to extract information from signals generated by heart sound sensors to detect valvular regurgitation (VR). Wavelet analysis decomposes an electrical signal with both frequency and time. Therefore, the signal energy information includes variations of the amplitude of the electrical signal with both frequency and time.

In wavelet analysis, a scalable modulated window is typically shifted along the time domain electrical signal and for every position the frequency spectrum is calculated. This process is typically repeated many times with a slightly shorter (or longer) window for every new cycle of the electrical signal. By using a variable width window, wavelet analysis effectively zooms in on the signal when analyzing higher frequencies, thus providing higher resolution when necessary. The result is a collection of time-frequency representations of the signal having different resolutions.

The time-frequency representations of the signal can then be decomposed into component signals. Many different wavelet functions can be used to decompose the input electrical signal into component parts. In some examples, Daubechies wavelets are used. The ability of a wavelet function to decompose a signal into its component parts depends on how closely the wavelet used approximates the electrical signal.

Figure 8:
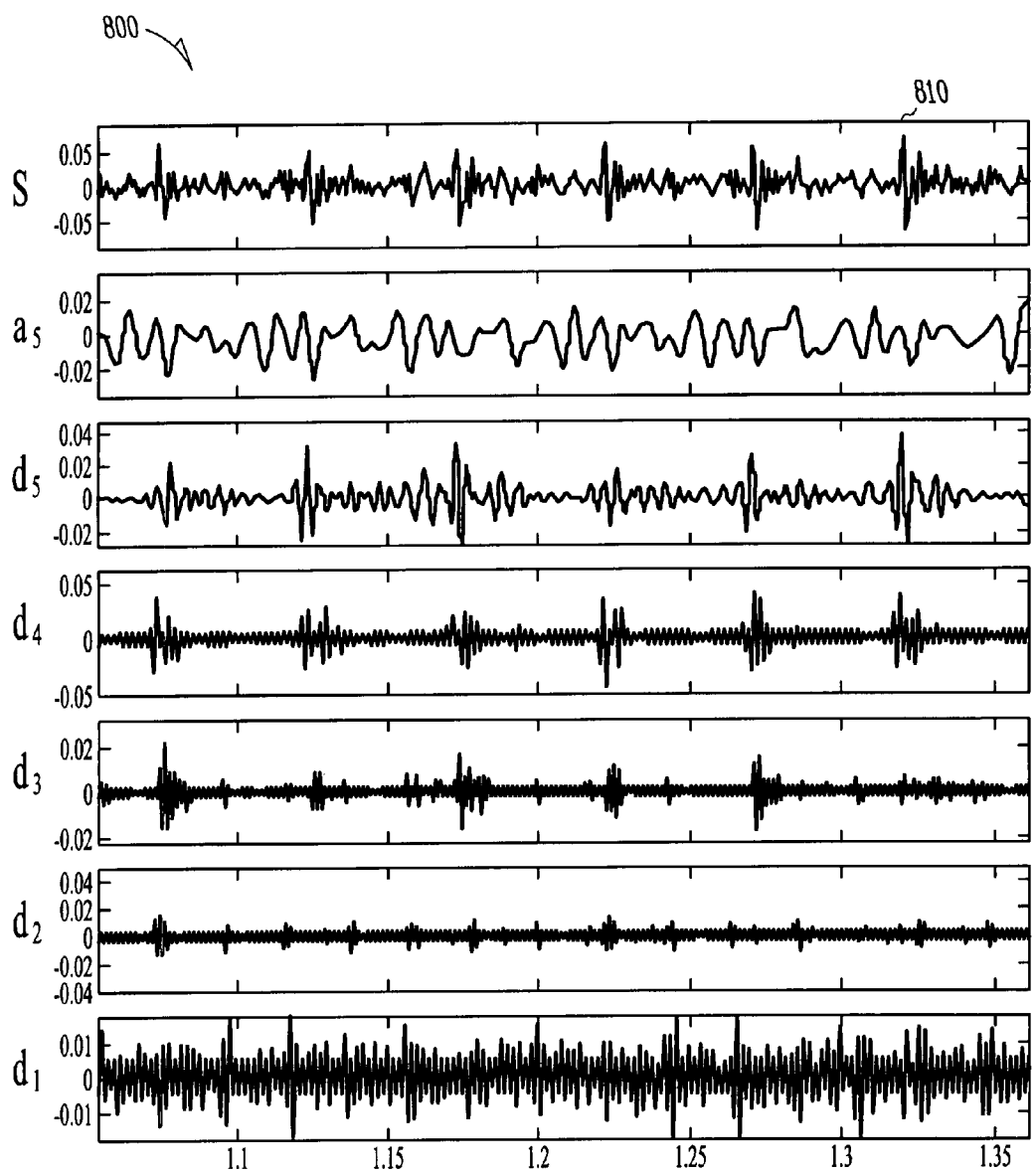
FIG. 8 shows graphical representations of the decomposition of an electrical signal obtained from a heart sound sensor.

FIG. 8 shows graphical representations 800 of the decomposition of the electrical signal obtained from the heart sound sensor. An electrical signal 810 is shown in the top graph. In this example, the decomposition is performed by running the electrical signal 810 through a bank of bandpass filters corresponding to the Daubechies wavelets to obtain the six individual decomposed element signals a5, d5, d4, d3, d2, and d1.

In some examples, the heart sound feature circuit 230 includes a wavelet filter circuit to decompose an electrical heart sound signal into component signals. Descriptions of systems and methods for monitoring heart sounds using wavelet filtering are found in Patangay et al., U.S. Patent Application Publication No. 20070123943, "Systems and Methods for Valvular Regurgitation Detection," filed Nov. 28, 2005, now issued as U.S. Pat. No. 8,108,034, which is incorporated herein by reference.

In some examples, once a feature is identified, the heart sound feature circuit 230 preprocesses subsequent heart sound signals (e.g., from subsequent cardiac cycles) by decomposing the heart sound signals into component signals. In certain examples, the heart sound feature circuit includes a threshold detector to detect one or more heart sound features of interest.

In some examples, the heart sound feature circuit 230 of FIG. 2 identifies heart sound signal features using a comparison to a heart sound template. The IMD 205 includes a memory to store one or more heart sound templates, which include previously attained heart sound information from the subject. The heart sound template includes at least one heart sound feature, such as a morphological feature. The heart sound feature circuit 230 uses a cross-correlation between a heart sound signal and at least a portion of the heart sound template to identify features in the heart sound signal. Descriptions of system and methods to identify heart sound features using a heart sound template are found in Patangay et al., U.S. patent application Ser. No. 11/736,055, "Heart Sound Tracking System and Method," filed Apr. 17, 2007, published as U.S. Patent Application Publication No. 20080262368, now issued as U.S. Pat. No. 7,853,327, which is incorporated by reference.

There may be difficulty in identifying features in heart sound signals for trending over subsequent cardiac cycles because variation in features may cause feature misdetections. A solution is to use information from previous and/or the current heart sound beat to reduce the misdetections. In some examples, the heart sound feature circuit 230 calculates a feature metric. A heart sound feature is tracked by optimizing the feature metric to find the most consistent heart sound feature or set of features. Descriptions of systems and methods to track heart sound features using optimization of a feature metric are found in the above mention Patangay et al., "Heart Sound Tracking System and Method."

Different pathologies of a patient may emphasize different individual components or features of heart sounds. As described above, a pathology may include a change to multiple heart sound features. Although detecting an occurrence of a heart sound, such as S1, may be relatively straightforward, determining which feature of the heart sound is the most sensitive to changes in systolic performance results in analyzing the heart sound complex over time. Because it is desired to find an optimum feature for trending, the physiologic perturbation is used to create a change in the features of the heart sound. When multiple heart sound signal features or components are identified, the identified candidate features can be ranked to determine which feature allows for correct and consistent physiologic variable measurements.

Figure 9:
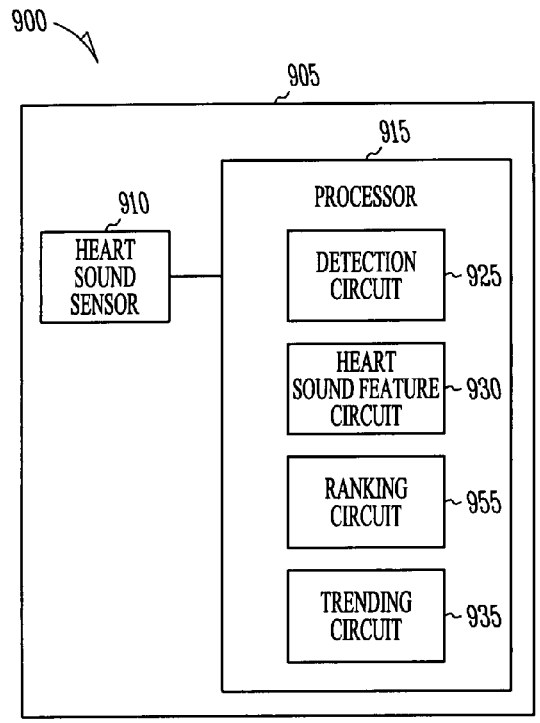
FIG. 9 shows a block diagram of portions of another example of a system for monitoring one or more heart sounds.

FIG. 9 shows a block diagram of portions of another example of a system 900 for monitoring one or more heart sounds. The system 900 includes an IMD 905 that in turn includes an implantable heart sound sensor circuit 910 and processor circuit 915. The processor circuit includes a detection circuit 925 to detect a physiologic perturbation and a heart sound feature circuit 930 to identify one or more heart sound features in the electrical heart sound signal. The processor circuit 915 is configured to trigger the heart sound feature circuit 930 in relation to a detected physiologic perturbation.

The processor circuit 915 also includes a ranking circuit 955 to rank identified candidate heart sound features and select a heart sound feature for trending according to the ranking. The ranking circuit 955 may rank the candidate features by giving a greater weight to candidate features of interest to the physiologic condition of the subject. For example, the ranking circuit 955 may give greater weight to a duration or width of the S1 heart sound when the physiologic condition of the subject relates to contractility and the IMD 905 is searching for a feature to trend contractility, than when the physiologic condition of the subject relates to drug therapy and the IMD 905 is searching for a feature to trend efficacy of the drug therapy.

According to some examples, the ranking circuit 955 uses a linear discriminant analysis classifier to rank the features. In certain examples, the linear discriminant analysis classifier uses Fischer's separability criterion to rank variables to train the classifier. In a regression problem where a set of inputs is used to predict an output variable, a correlation coefficient can be used to estimate the variability in the output due to a given input. A linear or non-linear fit can be used to calculate the correlation coefficient. Weighting can also be added to certain candidate features during the training of the classifier.

In some examples, the ranking circuit 955 uses entropy based (information theoretic) criteria to rank the candidate features. The estimated densities of discrete variables are used to calculate the mutual information between the input variables and the output to rank the candidate features. In some examples, the ranking circuit 955 ranks the candidate features using Chi-Square analysis. In some examples, the ranking circuit 955 ranks the candidate features using an analysis of variance (ANOVA) type statistical tests to rank the candidate features.

Once a heart signal feature or set of features to trend has been identified from the candidate features, the trending circuit 935 trends the heart sound feature in relation to a recurrence of the physiologic perturbation. The processor circuit 915 declares a change in a physiologic condition of the patient according to the trending.

Figure 10:
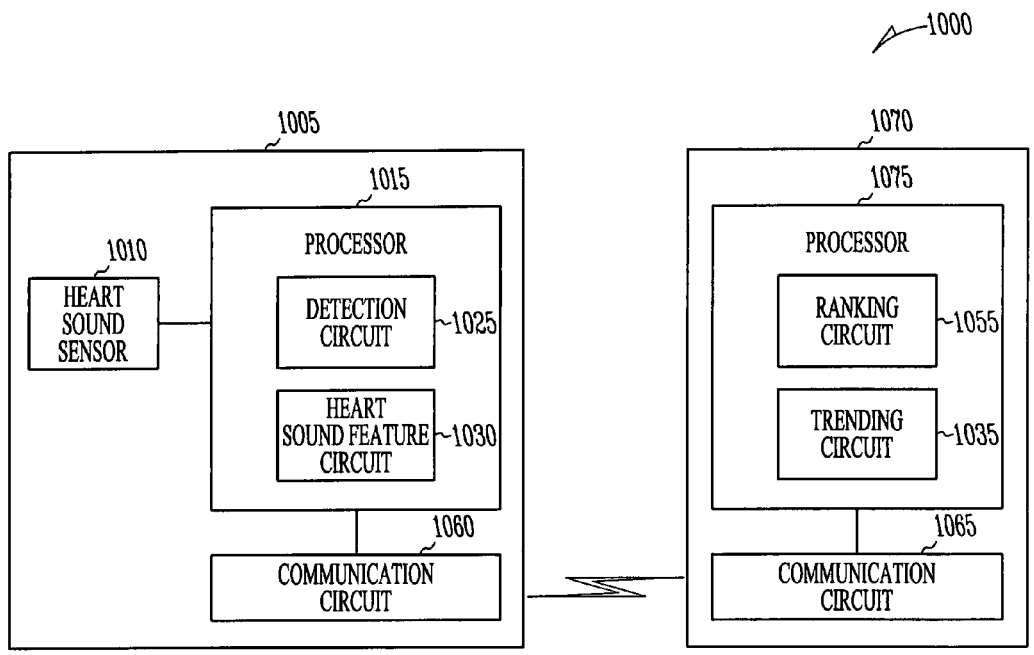
FIG. 10 shows a block diagram of portions of a further example of a system for monitoring one or more heart sounds.

In some examples, the trending and the ranking are done by a second device. FIG. 10 shows a block diagram of portions of another example of a system 1000 for monitoring one or more heart sounds. The system 1000 includes an IMD 1005 and an external device 1070. The IMD 1005 includes an implantable heart sound sensor circuit 1010 and a first processor circuit 1015. The processor circuit 1015 includes a detection circuit 1025 to detect a physiologic perturbation and a heart sound feature circuit 1030 to identify one or more heart sound features in the electrical heart sound signal. The processor circuit 1015 triggers the heart sound feature circuit 1030 in relation to a detected physiologic perturbation. The processor circuit 1015 communicates information about one or more heart sound signal features to the external device using the communication circuit 1060.

The external device 1070 includes a second processor circuit 1075 and communication circuit 1065 to communicate information with the IMD. Examples of the external device include an IMD programmer or a server. The IMD 1005 may communicate to the external device 1070 using a third device, such as a repeater for example. The processor circuit 1075 includes a trending circuit 1035 to trend the heart sound feature in relation to a recurrence of the physiologic perturbation. The processor circuit 1075 declares a change in a physiologic condition of the patient according to the trending. The processor circuit 1075 may provide an indication of the change to a user or a caregiver, such as by a display on the external device 1070 for example. The processor circuit 1075 may provide the indication to another process, such as a third device in communication with the external device via a communication network such as a computer network (e.g., the internet) or a cell phone network.

In some examples, the heart sound feature circuit 1030 of the IMD 1005 identifies a plurality of candidate heart sound features and the processor circuit 1015 communicates information about the heart sound signal features to the external device using the communication circuit 1060. The processor 1075 includes a ranking circuit 1055 to rank the candidate heart sound features and select a heart sound feature for trending according to the ranking.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
an implantable heart sound sensor circuit configured to produce an electrical heart sound signal representative of a heart sound of a subject;
a second implantable sensor circuit configured to produce a second electrical sensor signal related to one or more physiologic cardiovascular events in the subject;
a processor circuit coupled to the heart sound sensor circuit and the second sensor circuit, wherein the processor circuit includes:
  a heart sound feature circuit configured to identify a heart sound feature in the electrical heart sound signal in an absence of a physiologic perturbation;
  a detection circuit configured to detect the physiologic perturbation using the second electrical sensor signal, wherein the heart sound feature circuit is configured to identify the heart sound feature in the electrical heart sound signal in relation to the presence of the detected physiologic perturbation; and
  a trending circuit configured to trend a change in a difference between the heart sound feature in the presence of the physiologic perturbation and in the absence of the physiologic perturbation, and wherein the processor circuit is configured to declare a change in a physiologic condition of the patient according to the trend and provide an indication of the change to a user or process.

2. The system of claim 1, wherein the heart sound feature circuit is configured to identify a plurality of candidate heart sound features, wherein the processor circuit includes a ranking circuit configured to:
rank the candidate heart sound features; and
select a heart sound feature for trending according to the ranking 3. The system of claim 2, wherein the ranking circuit is configured to rank the candidate features according to a physiologic condition of the subject.

4. The system of claim 1, wherein the second implantable sensor circuit includes a cardiac signal sensing circuit configured to provide an electrical representative of an intrinsic cardiac signal of the subject, and wherein the detection circuit is configured to detect a premature ventricular contraction (PVC) to trigger the heart sound feature circuit.

5. The system of claim 1, wherein the second implantable sensor circuit includes an activity sensor to provide a signal representative of a physical activity level of the subject, and wherein the detection circuit is configured to detect that a physical activity level of the subject exceeds a threshold activity level from the signal to trigger the heart sound feature circuit.

6. The system of claim 1, wherein the second implantable sensor circuit includes a posture sensor, and wherein the detection circuit is configured to detect a change in posture of the subject to trigger the heart sound feature circuit.

7. The system of claim 1, wherein the second implantable sensor circuit includes a cardiac signal sensing circuit configured to provide an electrical representative of an intrinsic cardiac signal of the subject, and wherein the detection circuit is configured to detect that a heart rate of the subject exceeds a threshold heart rate to trigger the heart sound feature circuit.

8. The system of claim 1, wherein the second implantable sensor circuit includes a respiration sensor to provide a signal representative of respiration of the subject, and wherein the detection circuit is configured to detect a phase of a respiration cycle of the subject from the signal to trigger the heart sound feature circuit.

9. The system of claim 1, wherein the processor circuit includes a timer circuit, and wherein the processor circuit is configured to initiate the identification of the heart sound feature in relation to a time the subject receives a drug therapy.

10. The system of claim 1, wherein the processor circuit includes a timer circuit, and wherein the processor circuit is configured to initiate the identification of the heart sound feature in relation to a phase of a circadian cycle of the subject.

11. The system of claim 1, including a therapy circuit in electrical communication with the processor circuit, wherein the therapy circuit is configured to provide a therapy to the subject, and wherein the processor circuit is configured to initiate a therapy to cause the physiologic perturbation and to initiate the identification of the heart sound feature in a time relation to the therapy.

12. The system of claim 11, wherein the processor circuit is configured to initiate a paced cardiac contraction as the physiologic perturbation and initiate the identification of the heart sound feature in a time relation to the paced cardiac contraction.

13. The system of claim 12, wherein the processor circuit is configured to initiate a premature ventricular contraction (PVC) as the physiologic perturbation and to initiate the identification of the heart sound feature in a time relation to the PVC.

14. A method comprising:
implantably sensing an electrical heart sound signal representative of a heart sound of a subject;
identifying a feature in the heart sound signal in an absence of a physiologic perturbation;
implantably sensing a second electrical signal related to one or more physiologic cardiovascular events in the subject;
detecting the physiologic perturbation using the second signal;
identifying the feature of the heart sound signal in the presence of the detected physiologic perturbation;
trending a change in a difference between the heart sound feature in the presence of the physiologic perturbation and the heart sound feature in the absence of the physiologic perturbation;
identifying a change in a physiologic condition of the subject from the trending; and
providing an indication of the change to a user or process.

15. The method of claim 14, wherein identifying a feature includes:
identifying a plurality of candidate features of the heart sound signal;
ranking the candidate features; and
selecting a feature for trending according to the ranking.

16. The method of claim 15, wherein ranking the candidate features includes ranking the candidate features according to a physiologic condition of the subject.

17. The method of claim 14, wherein identifying a feature of the heart sound signal includes triggering identification of the feature of the heart sound in relation to a detected physiologic perturbation.

18. The method of claim 14, wherein identifying a feature of the heart sound signal includes triggering identification of the feature of the heart sound in relation to an induced physiologic perturbation.

19. The method of claim 14, wherein the physiologic perturbation is a premature ventricular contraction (PVC), and wherein sensing a heart sound signal includes sensing a heart sound signal in relation to the PVC.

20. The method of claim 14, wherein the physiologic perturbation is a change in posture of the subject, and wherein sensing a heart sound signal includes sensing a heart sound signal in relation to the change in posture.

21. The method of claim 14, wherein the physiologic perturbation is a heart rate of the subject exceeding a threshold heart rate, and wherein sensing a heart sound signal includes sensing a heart sound signal in relation to the heart rate of the subject exceeding the threshold heart rate.

22. The method of claim 14, wherein the physiologic perturbation is the subject receiving drug therapy, and wherein sensing a heart sound signal includes sensing a heart sound signal in relation to a time the subject receives the drug therapy.

23. The method of claim 14, wherein the physiologic perturbation is a paced cardiac contraction, and wherein sensing a heart sound signal includes sensing a heart sound signal in relation to the paced cardiac contraction.

24. The method of claim 14, wherein the physiologic perturbation is a phase of a respiration cycle, and wherein sensing a heart sound signal includes sensing a heart sound signal in relation to the phase of a respiration cycle.

25. The method of claim 14, wherein the physiologic perturbation corresponds to a circadian pattern, and wherein sensing a heart sound signal includes sensing a heart sound signal in relation to the circadian pattern.

26. The method of claim 14, wherein the physiologic perturbation includes activity of the subject exceeding a threshold activity level, and wherein sensing a heart sound signal includes sensing a heart sound signal in relation to the activity level of the subject exceeding the threshold activity level.

27. A system comprising:
- means for implantably sensing an electrical heart sound signal representative of a heart sound of a subject;
- means for identifying a feature in the heart sound signal in an absence of a physiologic perturbation;
- means for implantably sensing a second signal related to one or more physiologic cardiovascular events in the subject;
- means for detecting the physiologic perturbation using the second signal;
- means for identifying the heart sound feature in the presence of the detected physiologic perturbation;
- means for trending a change in a difference between the heart sound feature in the presence of the physiologic perturbation and the heart sound feature in the absence of the physiologic perturbation;
- means for identifying a change in a physiologic condition of the subject from the trending; and
- means for providing an indication of the change to a user or process.

28. A system comprising:
- an implantable medical device (IMD) including:
  - an implantable heart sound sensor circuit configured to produce an electrical heart sound signal representative of a heart sound of a subject;
  - a second implantable sensor circuit configured to produce a second electrical sensor signal related to one or more physiologic cardiovascular events in the subject;
  - a first processor circuit coupled to the heart sound sensor circuit and the second sensor circuit, wherein the processor circuit includes:
    - a heart sound feature circuit configured to identify a heart sound feature in the electrical heart sound signal in an absence of a physiologic perturbation;
    - a detection circuit configured to detect the physiologic perturbation using the second sensor signal, wherein the heart sound feature circuit is configured to identify the heart sound feature in the electrical heart sound signal in the presence of the detected physiologic perturbation; and
- an external device including:
  - a second processor circuit including a trending circuit configured to trend a change in a difference between the heart sound feature in the presence of the physiologic perturbation and in the absence of the physiologic perturbation, wherein the second processor circuit is configured to declare a change in a physiologic condition of the subject according to the trending and provide an indication of the change to a user or process.

29. The system of claim 28, wherein the heart sound feature circuit is configured to identify a plurality of candidate heart sound features, wherein the first processor circuit is configured to communicate information about the heart sound signal features to the external device; and wherein the second processor circuit includes a ranking circuit configured to:
- rank the candidate heart sound features; and
- select a heart sound feature for trending according to the ranking.

30. The system of claim 29, wherein the ranking circuit is configured to rank the candidate features according to a physiologic condition of the subject.

* * * * *